United States Patent [19]

Wilcher et al.

[11] Patent Number: 5,081,086
[45] Date of Patent: * Jan. 14, 1992

[54] SOLID PHOSPHORIC ACID CATALYST

[75] Inventors: Fiona P. Wilcher, Des Plaines; Tai-Hsiang Chao, Mt. Prospect, both of Ill.

[73] Assignee: UOP, Des Plaines, Ill.

[*] Notice: The portion of the term of this patent subsequent to Aug. 7, 2007 has been disclaimed.

[21] Appl. No.: 451,978

[22] Filed: Dec. 18, 1989

Related U.S. Application Data

[62] Division of Ser. No. 290,477, Dec. 29, 1988, Pat. No. 4,912,279.

[51] Int. Cl.$^5$ .............. B01J 21/16; B01J 27/182; B01J 37/28
[52] U.S. Cl. ...................... 502/81; 502/80; 502/214
[58] Field of Search ............. 502/214, 80, 81; 585/529, 466

[56] References Cited

U.S. PATENT DOCUMENTS

| | | | |
|---|---|---|---|
| 2,116,151 | 3/1938 | Ipatieff et al. | 502/214 |
| 2,275,182 | 3/1942 | Ipatieff et al. | 502/214 |
| 2,586,852 | 2/1952 | Morrell | 585/529 |
| 2,960,477 | 11/1960 | Smith | 502/214 |
| 3,044,964 | 7/1962 | Morrell | 502/64 |
| 3,050,470 | 8/1962 | Morrell | 502/214 |
| 3,520,945 | 7/1970 | Graff | 585/466 |
| 3,527,823 | 9/1970 | Jones | 585/447 |
| 3,551,510 | 12/1970 | Pollitzer et al. | 585/466 |
| 3,661,801 | 5/1972 | Gutmann et al. | 585/529 |
| 4,617,070 | 10/1986 | Dreibelbis | 106/193 R |
| 4,912,297 | 3/1990 | Wilcher et al. | 585/466 |
| 4,946,815 | 8/1990 | Chao et al. | 502/85 |

*Primary Examiner*—Paul E. Konopka
*Attorney, Agent, or Firm*—Thomas K. McBride; Eugene I. Snyder

[57] ABSTRACT

A novel solid phosphoric acid catalyst composition is disclosed. The composite comprises solid phosphoric acid and a refractory oxide binder. The composite is characterized in that 25.0 volume percent or less of the total catalyst pore volume consists of pores having a diameter of 10,000 Å or greater. An improvement in catalyst activity and stability is observed when such a catalyst is utilized in a hydrocarbon conversion process.

8 Claims, No Drawings

SOLID PHOSPHORIC ACID CATALYST

CROSS-REFERENCE TO RELATED APPLICATIONS

This application is a division of prior copending application Ser. No. 290,477 filed Dec. 29, 1988, now U.S. Pat. No. 4,912,279.

BACKGROUND OF THE INVENTION

This invention relates to a solid phosphoric acid catalyst composite that is characterized in that 25.0 percent or less of the total catalyst pore volume consists of pores having a diameter of 10,000 Å or greater.

Solid phosphoric acid is the name which has come into use for a calcined mixture of an acid of phosphorus and a porous binder material such as kieselguhr, infusorial earth, and diatomaceous earth. Solid phosphoric acid catalysts for years have been virtually the only catalysts effective in the polymerization of normally gaseous olefins to form normally liquid hydrocarbons. Mixtures of propane and propylene, butane and butylene, and ethane and ethylene are the chief feedstocks to the polymerization process. Additionally, solid phosphoric acid catalysts are very useful in catalyzing the alkylation of aromatic hydrocarbons with aliphatic hydrocarbons. Especially for alkylating benzene with propylene to produce cumene.

DESCRIPTION OF THE PRIOR ART

Solid phosphoric acid catalysts that have certain properties, additives, formulations, and the like are well known in the art to provide a stronger, more active, and longer lasting catalyst. However, a solid phosphoric acid catalyst composite characterized in that 25.0 percent or less of the total catalyst composite pore volume consists of pores having a diameter of 10,000 Å or larger and exhibiting improved stability in a catalytic condensation reaction has heretofore been unknown.

Basic recipes for solid phosphoric acid catalyst composites are well known and disclosed for example in U.S. Pat. No. 2,586,852 which describes a solid phosphoric acid comprising a mixture of kaolin, a crystalline silica, and phosphoric acid.

Porous binder materials have been known to improve the performance characteristics of a solid phosphoric acid catalyst composite. U.S. Pat. No. 3,044,964 describes a solid phosphoric acid catalyst composite comprising phosphoric acid and a natural porous silica material. In addition, this catalyst could comprise binders that were not naturally porous.

The optimization of a solid phosphoric acid catalyst on the basis of pore volume is relatively unknown in the art. U.S. Pat. No. 3,661,801 was the sole reference discovered which discloses a solid phosphoric acid catalyst composite manufactured to obtain a specific pore volume distribution. The catalyst disclosed has from 0.2 to 0.4 cc/g of pores greater than 350 Å in diameter and from 0.07 to 0.20 cc/g of pores greater than 9,000 Å in diameter. Therefore, at minimum, the percentage of catalyst pore volume of this prior art catalyst that is comprised of pores greater than 9,000 Å is 17.5 percent or more or 0.07 cc/g in absolute amounts. Additionally, such a catalyst has been disclosed as being manufactured by a method which results only in a spherically shaped catalyst. All of these factors distinguish the catalyst prepared by the method disclosed in the '801 patent from the catalyst of this invention.

U.S. Pat. No. 3,520,945 teaches the art of maintaining proper control of water injection into the reaction zone of alkylation and oligomerization processes, including those processes that utilize solid phosphoric catalyst.

U.S. Pat. No. 3,527,823 teaches the practice of operating a two-phase alkylation reaction zone with net flow upwards through the reactor and in the presence of an unreactive vapor dispersant.

U.S. Pat. No. 3,551,510 teaches that an alkyl aromatic compound may be produced by the steps of alkylation, transalkylation, and separation.

OBJECTS AND EMBODIMENTS

A principal objective of this invention is to provide an improved solid phosphoric acid catalyst. The improved catalyst exhibits enhanced stability in comparison to similar catalysts of the prior art. This improvement in activity and stability is due to the unique pore volume distribution of the instant catalyst.

Accordingly, a broad embodiment of the present invention is a solid phosphoric acid catalyst composite. The solid phosphoric acid catalyst composite comprises solid phosphoric acid and a binder material. The catalyst is characterized in that 25.0 percent or less of the total catalyst composite pore volume consists of pores having a diameter of 10,000 Å or larger. The solid phosphoric acid catalyst composite is further characterized in that the binder material is preferably an inorganic oxide material and most preferably a siliceous material such as diatomaceous earth, kieselguhr, or artificially prepared silicas or mixtures thereof.

In a preferred embodiment, the solid phosphoric acid catalyst composition is in the form of an extrudate and comprises phosphoric acid and an inorganic oxide binder. The preferred catalyst is characterized in that 17.5 percent or less of the catalyst composite extrudate pore volume consists of pores having diameters of 10,000 Å or larger. The catalyst is further characterized in that the total catalyst composite extrudate pore volume is about 0.28 cc/g or less with the absolute pore volume for the pores having diameters of 10,000 Å or larger being 0.07 cc/g or less. Finally, it is preferred that the instant catalyst composite comprise at least 60 wt. % $P_2O_5$.

DETAILED DESCRIPTION OF THE INVENTION

Solid phosphoric acid catalysts are well known for their utility in various important hydrocarbon conversion processes. However, there have always been problems associated with the use of a solid phosphoric acid catalyst in such processes including catalyst dissolution, poor catalyst physical strength, poor catalyst stability, and the like. Therefore, strong catalysts exhibiting high activity and stability are always being pursued. To approach this goal of manufacturing a strong, high activity, long-life catalyst, we have found that pore volume is a critical factor in the stability of a solid phosphoric acid with the reduction in macropore volume, i.e. pores greater than 10,000 Å in diameter, being of great importance.

It is a critical aspect of this invention that the catalyst comprise 25.0 percent or less of its pore volume in pores greater than 10,000 Å in diameter. It is most preferred that pores of 10,000 Å or greater make up only 17.5 percent or less of the total catalyst pore volume. It is believed that the large amount of macropore volume not only weakens the strength of the extrudates but also increases the carbon buildup during usage caused by the enhanced pore diffusion by macroporosity. Higher carbon buildup during the reaction could potentially lead to faster catalyst deactivation and catalyst swelling to cause higher than normal reactor pressure drop.

In addition, it has been observed that total pore volume of the catalyst is also related to catalyst stability. Therefore, it is preferred that the total catalyst pore volume is at most 0.28 cc/g and preferably at most 0.23 cc/g.

The essential and active ingredient of the solid phosphoric acid catalyst herein contemplated is an acid of phosphorus, preferably one in which the phosphorus has a valence of +5. The acid may constitute from about 60 to about 80 wt. % or more of the catalyst mixture ultimately produced. Of the various acids of phosphorus, orthophosphoric acid ($H_3PO_4$) and pyrophosphoric acid ($H_4P_2O_7$) find general application in the primary mixtures, due mainly to their cheapness and to the readiness with which they may be procured, although the catalyst composite produced is not restricted to their use but may employ any of the other acids of phosphorus insofar as they are adaptable. It is not intended to infer, however, that the different acids of phosphorus, which may be employed will produced catalyst which have identical affects upon any given organic reactions as each of the catalysts produced from different acids and by slightly varied procedure will exert its own characteristic action. However, it is believed that the catalyst produced as disclosed herein will have superior hydrocarbon conversion properties in comparison to catalysts without the pore volume distribution disclosed herein.

In using orthophosphoric acid as a primary ingredient, different concentrations of the aqueous solution may be employed from approximately 75 percent to 100 percent. An acid containing some free phosphorus pentoxide may even be used. By this is meant that the ortho acid may contain a definite percentage of the pyro acid corresponding to the primary phase of dehydration of the orthophosphoric acid. Within these concentration ranges, the acids will be liquids of varying viscosities, and will readily mix with adsorbent materials. In practice, it has been found that pyrophosphoric acid corresponding to the formula $H_4P_2O_7$ can be incorporated with binder materials at temperatures somewhat above its melting point (61° C.) and that the period of heating which is given to the pyro acid adsorbent mixtures may be different from that used when the ortho acid is so employed.

Triphosphoric acid which may be represented by the formula $H_5P_3O_{10}$ may also be used as a starting material for preparation of the catalyst of this invention. These catalytic compositions may also be prepared from the siliceous materials mentioned herein and phosphoric acid mixtures containing orthophosphoric, pyrophosphoric, triphosphoric, and other polyphosphoric acids.

The binder material which may be employed as a component of the solid phosphoric acid catalyst composite may be any material that is able to adsorb or bind with the phosphoric acid component of the catalyst composite. One such group of material is refractory inorganic oxides such as alumina, silica, or other metal oxides such as oxides of magnesium, calcium, phosphorus, and titanium, or mixtures thereof to name but a few.

It is preferred that the binder material be a siliceous material. Examples of such siliceous or $SiO_2$-containing materials which are useful as the binder component of the instant solid phosphoric acid catalyst include kieselguhr, diatomaceous earth, infusorial earth, kaolin, fullers earth, or artificially prepared porous silica or mixtures thereof. It is most preferred that the siliceous binder material is kieselguhr. However, it is noted that the terms infusorial earth, kieselguhr, and diatomaceous earth and in general such naturally occurring porous siliceous materials will be used and referred to interchangeably and on an equivalent basis in general in connection with the present invention.

One method that may be used to produce a solid phosphoric acid catalyst composite having the desired pore volume characteristics of the catalyst of this invention is to closely control the particle size of the binder material. Most binder materials typically contain particles varying greatly in size. It is anticipated that by using very small sized particles of binder material, the resulting solid phosphoric acid catalyst composite will be more compact and will thus contain fewer pores greater than 10,000 Å in diameter, in comparison to a catalyst that was manufactured with larger binder particles.

Small binder particles can be obtained in a variety of manners. The binder material can be classified with screens to capture only the smallest particles. Alternatively, the binder materials can be mechanically sized using an Eiger mill, or a ball mill, or the like to break the larger particles into smaller particles useful in the instant solid phosphoric acid catalyst composite. If binder classification is used to produce the catalyst of the instant invention, then it is preferred that the binder material particle size ranges from 1 to about 150 microns.

In producing the catalyst composites which are utilized in the present invention, an oxygen acid of phosphorus and the solid binder material described above are mixed at a temperature of from about 10° to about 232° C. and preferably at a temperature of from about 95° to about 180° C. to form a composite. Thus, satisfactory results have been obtained by heating polyphosphoric acid (82% $P_2O_5$ content) at a temperature of about 170° C. and then mixing this hot acid with diatomaceous earth which has previously been at room temperature. The polyphosphoric acid and diatomaceous earth form a composite in which the weight ratio of phosphorus pentoxide to diatomaceous adsorbent is from about 1.5 to about 7.5. This composite is slightly moist to almost dry in appearance but becomes plastic when subjected to pressure in a hydraulic press-type or auger-type extruder by which the composite is formed into pieces that are cut into shaped particles.

The extrusion of the phosphoric acid/binder mixture is another step in the catalyst manufacturing process in which the porosity of the catalyst composite can be optimized to reduce the amount of pores greater than 10,000 Å in the catalyst composite. Extrusion may be used to control catalyst porosity in a number of ways essentially by controlling extrusion back-pressure. Generally, the greater the extrusion pressure, the more compact or the lower the porosity, pore volume, and pore diameter of the catalyst. Extrusion back-pressure can be varied by a variety of methods. One method is to vary the cross-sectional area of holes in the extruder die plate. Another method is to vary the moisture content of the dough being extruded with a drier dough creating more back-pressure. A further method is related to the intensity or energy exerted in extruding the instant catalyst composite. An extrudate may be produced in an extrusion apparatus that comprises a screw that rotates, or that comprises a ram. Both types of apparatuses compact the dough before extrusion through the die plate. By varying screw speed or ramming intensity along with other extrusion variables, such as screw-to-barrel clearances, screw pitch, and the like, more extrusion energy can be expended in compacting and extruding the catalyst precursor dough.

What is important about the extrusion variables and other variables affecting the catalyst is that: (1) the desired catalyst porosity distribution is known; and (2) extrusion and other process variables affecting the finished catalyst are understood and can be controlled. Those familiar with extrusion will certainly understand the contribution of the variables listed above in controlling the extended catalyst porosity and will therefore be able to control such variables to consistently produce a solid phosphoric acid catalyst of this invention.

It is finally preferred that the solid phosphoric acid catalyst of this invention is manufactured in the form of an extrudate. It is believed that the instant catalyst can be manufactured in many shapes with the requisite pore diameter/pore volume distribution. However, it is felt that such important properties will be easier to control if the catalyst composite is in extrudate form. Also, extrusion is typically an efficient and cheap method of producing a formed catalyst particle.

The catalyst composite formed, for example by extrusion, is amorphous (or green) and must undergo a crystallization step that places the catalyst composite in a crystalline form ready for use in a hydrocarbon conversion process. Typically, the crystallization step is calcination. The calcination of the amorphous extrudate may be accomplished in any known calcination process of the prior art which controls temperature and time, and optionally, moisture level in the calcination zone. Thus, the crystallization of the catalyst may occur in a calcination apparatus containing a single calcination zone, two calcination zones, or three or more calcination zones. A calcination zone is characterized in that at least the temperature of the zone can be controlled independently of the other calcination zones.

The calcination variables noted above are believed to directly impact on the final type and amount of ores and pore volume in the calcined solid phosphoric acid catalysts. As mentioned, it is preferred that the finished solid phosphoric acid catalyst be characterized in that 25.0 percent or less of the total catalyst pore volume consists of pores having a diameter of 10,000 or larger. Further, it is preferred that the catalyst have a total pore volume of 0.28 cc/g or less.

Temperature is a first critical calcination condition. Temperature is important in both dehydrating the amorphous material and in controlling the type of crystallites produced as a result of the calcination. It is well known that high calcination temperatures, especially those above 500° C. result in a solid phosphoric acid catalyst comprising essentially only crystallites of silicon pyrophosphate. As a result of desiring a catalyst with crystallites of both silicon orthophosphate and silicon pyrophosphate, it was determined that calcination temperatures ranging from 100° to 450° C. were most desirable and especially calcination temperatures between 350° and 450° C.

In conjunction with controlling calcination temperature, it is known that the steam, or moisture, content of the calcination zone can be controlled closely to produce a finished solid phosphoric acid catalyst composite exhibiting the desired porosity and pore volume. It is desired that the steam content of the vapor of the calcination zone or zones be greater than 5.0 mole percent based upon the total vapor rate to the calciner to impart the desired porosity characteristics into the instant catalyst.

It should be noted that controlling the steam content of the calciner vapors does not necessarily mean that all or even part of the steam to the calciner must be added from an outside source. It is quite possible that much of the steam will be present in the vapor in the calcination zone as a result of evaporation of water from the catalyst during the calcination. Steam addition to the calcination zone or zones will likely be required but the variable might also be controlled by controlling such variables as total vapor rate through the calcination zone or zones, temperature, and green catalyst moisture content among others.

Time in the calciner is also an important variable. Typically, the total calcination time will vary from 20 to 120 minutes. When more than one calcination zone is used, the total time in each may vary such that the total calcination time ranges from 20 to 120 minutes.

It is a further preferred aspect of this invention that where there is more than one calcination zone, at least one calcination zone must be operated at the conditions above. It is further preferred that the terminal (or final) calcination zone in a multiple calcination zone calciner is operated at the desired process conditions detailed above. This is not to say that other calcination zones besides the terminal zone cannot be operated at the preferred operating conditions, but it is believed that operating the final calcination zone at the highest temperature is the most efficient way of producing the catalyst disclosed herein.

In addition, it is preferred that the moisture level in the terminal calcination zone be 5.0 mole percent or greater. A solid phosphoric acid catalyst calcined by the method above will generally have the desired porosity as described hereinabove. As a result, 25.0 percent or less of its total pore volume of the instant catalyst composite will comprise pores of 10,000 Å or greater as analyzed by the mercury intrusion method.

The catalyst surface area and pore volume distribution are typically determined by mercury intrusion and extrusion methods. The mercury intrusion and extrusion methods are widely used in the catalysis science for catalyst porosity characterization. Detail discussion can be found in literature references such as *A Review of Mercury Porosimetry* by H. M. Rootare in Advanced Experimental Techniques in Powder Metallurgy, pp 225–252, Plenum Press, 1970, *A Generalized Analysis for Mercury Porosimetry* by R. W. Smithmick in Powder Technology, 33 (1982) pp 201–209, and *Advances in Experimental Techniques for Mercury Intrusion Porosimetry* by D. N. Winslow in Surface Colloid Science, vol. 13.

The catalyst of this invention is useful in catalytic condensation, aromatic alkylation, and other types of hydrocarbon conversion processes where solid phosphoric acid catalysts have been known to be useful. When employed in the conversion of olefinic hydrocarbons into polymers, the catalyst formed as heretofore set forth, is preferably employed as a granular layer in a heated reactor which is generally made from steel, and through which the preheated hydrocarbon fraction is directed. Thus, the solid catalyst of this process may be employed for treating mixtures of olefin-containing hydrocarbon vapors to effect olefin polymerization, but the same catalyst may also be used at operating conditions suitable for maintaining liquid phase operation during polymerization of olefinic hydrocarbons, such as butylenes, to produce gasoline fractions.

When used for polymerizing normally gaseous olefins, the particles of the catalyst are generally placed in vertical cylindrical treating towers or in fixed beds in reactors or towers and the gases containing olefins are passed downwardly through the reactors or towers at temperatures of 170° to 290° C. and pressures of 6 to 102 atmospheres. These conditions are particularly applicable when dealing with olefin-containing material which may contain from approximately 10 to 50 percent or more or propylene and butylenes. When operating on a mixture comprising essentially propylene and butylenes, this catalyst is effective at temperatures from about 140° to about 250° C. and at a pressure of from about 34 to about 102 atmospheres.

The catalyst of this invention is also useful in the alkylation of aromatic hydrocarbons with an alkylating agent. The alkylating agent which may be charged to the alkylation reaction zone may be selected from a group of diverse materials including monoolefins, diolefins, polyolefins, acetylenic hydrocarbons, and also alkylhalides, alcohols, ethers, esters, the latter including the alkylsulfates, alkylphosphates, and various esters of carboxylic acids. The preferred olefin-acting compounds are olefinic hydrocarbons which comprise monoolefins containing one double bond per molecule. Monoolefins which may be utilized as olefin-acting compounds in the process of the present invention are either normally gaseous or normally liquid and include ethylene, propylene, 1-butene, 2-butene, isobutylene, and the higher molecular weight normally liquid olefins such as the various pentenes, hexenes, heptenes, octenes, and mixtures thereof, and still higher molecular weight liquid olefins, the latter including various olefin polymers having from about 9 to about 18 carbon atoms per molecule including propylene trimer, propylene tetramer, propylene pentamer, etc. Cycloolefins such as cyclopentene, methylcyclopentene, cyclohexene, methylcyclohexene, etc., may also be utilized, although not necessarily with equivalent results. Other hydrocarbons such as paraffins, naphthenes, and the like containing 2 to 18 carbon atoms may also be present in the alkylating agent. When the catalyst of the present invention is used for catalyzing an aromatic alkylation reaction, it is preferred that the monoolefin contains at least 2 and not more than 14 carbon atoms. More specifically, it is preferred that the monoolefin is propylene.

The aromatic substrate which is charged to the alkylation reaction zone in admixture with the alkylating agent may be selected from a group of aromatic compounds which include individually and in admixture, benzene and monocyclic alkyl-substituted benzene of from 7 to 12 carbon atoms having the structure:

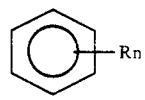

where R is methyl, ethyl, or a combination thereof, and n is an integer from 1 to 5. In other words, the aromatic substrate portion of the feedstock may be benzene, an alkylaromatic containing from 1 to 5 methyl and/or ethyl group substituents, and mixtures thereof. Nonlimiting examples of such feedstock compounds include benzene, toluene, xylene, ethylbenzene, mesitylene (1,3,5-trimethylbenzene) and mixtures thereof. It is specifically preferred that the aromatic substrate is benzene.

In a continuous process for alkylating aromatic hydrocarbons with olefins, the previously described reactants are continuously fed into a pressure vessel containing solid phosphoric acid catalyst of this invention. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably from about 2:1 to 8:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor.

In some cases, in order to maintain the reaction temperature in the preferred range and thus reduce the formation of unwanted polyalkylaromatics, it may be desirable to quench the reactants to dissipate heat of reaction. A quench stream comprised of the alkylating agent olefin, the alkylating agent or a portion of the reactor effluent stream, or mixtures thereof may be injected into the alkylation reactor system in order to dissipate heat and supply additional amounts of olefin alkylating agent and unreacted aromatic substrate at various locations within the reaction zone. This is accomplished for example in a single-stage reactor by multiple injection of the aforementioned quench stream components into the reaction zone via strategically placed inlet lines leading into said reaction zone. The amount and composition of quench material injected into either a single stage reaction system or multi-stage reaction system may be varied according to need. Benefits resulting from multiple quench injection include elimination of costly cooling apparatus in the process, improved selectivity to formation of the desired alkylaromatic compound, provision for a larger heat sink and optimization of the olefin to aromatic compound molar ratio throughout the reaction zone, thus resulting in increased yield of the desired monoalkylated aromatic compound.

Temperatures which are suitable for use in the process herein are those temperatures which initiate a reaction between an aromatic substrate and the particular olefin used to selectively produce the desired monoalkylaromatic compound. Generally, temperatures suitable for use are from about 100° to about 390° C., especially from about 150° to about 275° C. Pressures which are suitable for use herein preferably are above about 1 atmosphere but should not be in excess of about 130 atmospheres. An especially desirable pressure range is from about 10 to about 40 atmospheres; with a liquid hourly space velocity (LHSV) based upon the benzene feed rate of from about 0.5 to about 50 hr$^{-1}$, and especially from about 1 to about 10 hr$^{-1}$. It should be noted that the temperature and pressure combination used herein is to be such that the alkylation reaction takes place in essentially the liquid phase. In a liquid phase process for producing alkylaromatics, the catalyst is continuously washed with reactants, thus preventing buildup of coke precursors on the catalyst. This results in reduced amounts of carbon forming on said catalyst in which case, catalyst cycle life is extended as compared to a gas phase alkylation process in which coke formation and catalyst deactivation is a major problem.

Additionally, a regulated amount of water is preferably added to the alkylation reaction zone. In order to substantially prevent loss of water from the catalyst and subsequent decrease in catalyst activities, an amount of water or water vapor such as steam is added to the charge so as to substantially balance the water vapor pressure of the alkylation catalyst hereinabove described. This amount of water varies from about 0.01 to 6% by volume of the organic material charged to the alkylation reaction zone. The water is then typically removed with the light by-product stream recovered in the first separation zone.

A substantial portion of the aromatic substrate hydrocarbon and essentially all of the olefin alkylating agent react in the alkylation reaction zone in the presence of the solid phosphoric acid catalyst to form monoalkylaromatic compounds and polyalkylaromatic compounds. The preferred product of an alkylation process utilizing the solid phosphoric acid catalyst composite of this invention is cumene.

The following examples are presented to illustrate the catalyst composite and uses of the catalyst of the present invention and are not intended as an undue limitation on the generally broad scope of the invention as embodied in the claims.

EXAMPLE I

This example illustrates the general preparation method for the amorphous form phosphoric acid catalyst extrudate that is converted by various calcination methods of the subsequent examples into crystalline forms of solid phosphoric acid catalyst with different amounts of macropore volume.

Kieselguhr clay and phosphoric acid having a $P_2O_5$ content of 82% or greater were combined at a weight ratio of 1 to 2 at a temperature of 170° C. This material was extruded with an extruder through a die to produce extrudates with approximately 5 mm diameter. Only material with an amorphous character was detected by x-ray analysis of the green extrudates. The extrudates thus produced were then used in the calcination experiments described in the following Examples II to V. The calcination conditions include temperatures of from 100° C. to 500° C., moisture levels of from 0 to 25 mole percent based upon the total vapor rate to the calciner, all for a time ranging from 20 to 120 minutes. The final catalysts were analyzed for porosity and pore volume distribution. The pore volume distribution was measured by mercury intrusion with a Micromeritic Autopore 9220.

EXAMPLE II

This example highlights the effect that various calcination conditions have on the porosity and pore volume distribution of solid phosphorus acid catalysts. A batch of amorphous solid phosphoric acid green extrudates from Example I was subjected to a calcination process in a small furnace in batches of 100 to 150 grams. The furnace contained a means of allowing once through air and steam to be added at a control rate as well as a means for closely controlling the furnace temperature. After about 50 minutes under only a 3% steam rate in a furnace which has been preheated to 392° C. furnace temperature the catalyst was removed and analyzed for its porosity. The calcined catalyst had a total pore volume of 0.236 cc/g and macropore volume (pore volume greater than 10,000 Å) of 0.071 cc/g as measured by mercury intrusion. The macropore volume therefore represents 30% of the total pore volume. This catalyst does not fit the definition of the catalyst of this invention.

A second batch of amorphous solid phosphoric acid green extrudates from Example I was subjected to a calcination process in the same small oven as in the Example II. After about 50 minutes under 14% steam rate in a furnace which has been preheated to 430° C. temperature followed by 22% steam addition rate for 20 minutes, the catalyst was removed and analyzed for its porosity. The total pore volume of 0.239 cc/g and macropore volume (pore volume greater than 10,000 Å of 0.035 cc/g were measured by mercury intrusion method. This macropore volume represents 15% of the total pore volume. This catalyst falls within the porosity/pore volume distribution of the catalyst of this invention. It is evident from the example that steam rate to the calcination zone is critical in producing a catalyst with the porosity and pore volume distribution of this invention.

EXAMPLE III

A number of solid phosphoric acid catalysts prepared essentially as set forth in Example I were analyzed for total pore volume and pore volume distribution by mercury intrusion method. This results of this analysis can be found in Table 1 below.

The analyzed catalysts were then tested for catalyst life by placing the catalysts in an olefin polymerization process plant with propylene feed. The test was conducted under 68 atmospheres pressure, at a hydrocarbon feed space velocity of from 1.8 to 2.1, and at a temperature from 150° to 230° C. The testing occurred in a plant operated at constant conversion directed towards making a commercial product. The catalyst life values are all reported relative to catalyst E which had the shortest catalyst life. The end of the catalyst's life was determined when the pressure drop across the catalyst bed became too great to continue processing.

TABLE 1

| Catalyst | A | B | C | D | E |
|---|---|---|---|---|---|
| Catalyst Life (gal/lb) | 2.43 | 1.84 | 1.50 | 1.48 | 1.0 |
| Total Pore Volume (cc/g) | 0.183 | 0.215 | 0.197 | 0.187 | 0.212 |
| Pore Volume >10,000 Å (cc/g) | 0.027 | 0.042 | 0.045 | 0.046 | 0.048 |
| % of Volume >10,000 Å | 14.7 | 19.5 | 22.8 | 24.6 | 22.6 |

The data above indicates that there is a definite correlation between catalyst life and the percentage of volume of pores above 10,000 Å in a solid phosphoric acid catalyst. The correlation indicated is that the lower the percentage of the catalyst volume contained in pores above 10,000 Å in diameter, the greater the catalyst life.

What is claimed is:

1. A solid phosphoric acid composite comprising one or more acids of pentacovalent phosphorus in an amount from about 60 to about 88 weight percent of the composite, adsorbed on a binder which is a refractory inorganic oxide or a siliceous material, said composite having a pore volume no more than 0.28 cc/g with 25 percent or less of the pore volume arising from pores with a diameter greater than 10,000 Å.

2. The solid phosphoric acid composite of claim 1 where the refractory inorganic oxide is selected from the group consisting of alumina, magnesium oxide, calcium oxide, titanium oxide, and phosphorus oxides.

3. The solid phosphoric acid composite of claim 1 where the siliceous material is selected from the group consisting of silicas, kieselguhr, diatomaceous earth, infusorial earth, kaolin, fullers earth, or combinations thereof.

4. The solid phosphoric acid composite of claim 3 where the siliceous material is diatomaceous earth, kieselguhr, an artificially prepared porous silica, or combinations thereof.

5. The solid phosphoric acid composite of claim 1 where the pore volume of the composite is no more than about 0.23 cc/g.

6. The solid phosphoric acid composite of claim 1 where 17.5 percent or less of the pore volume arises from pores with a diameter greater than 10,000 Å.

7. The solid phosphoric acid composite of claim 1 where the pore volume of the composite is no more than about 0.23 cc/g. and 17.5 percent or less of the pore volume arises from pores with a diameter greater than 10,000 Å.

8. The solid phosphoric acid composite of claim 1 in the form of an extrudate.

* * * * *